United States Patent [19]

Umemura et al.

[11] 4,338,471

[45] Jul. 6, 1982

[54] PROCESS FOR PREPARING PHENOL

[75] Inventors: Sumio Umemura; Ryozo Kitoh; Taizo Uda, all of Ube, Japan

[73] Assignee: Ube Industries, Inc., Ube, Japan

[21] Appl. No.: 217,116

[22] Filed: Dec. 17, 1980

[30] Foreign Application Priority Data

Dec. 19, 1979 [JP] Japan ................................ 54-164022

[51] Int. Cl.³ ...................... C07C 37/58; C07C 39/04
[52] U.S. Cl. .................................. 568/802; 568/800
[58] Field of Search ...................... 568/802, 771, 800

[56] References Cited

U.S. PATENT DOCUMENTS

| 2,776,317 | 5/1957 | Reeder | 568/802 |
| 3,033,903 | 5/1962 | Loeb | 568/802 |
| 3,415,885 | 12/1968 | Hooper | 568/802 |

FOREIGN PATENT DOCUMENTS

| 1942386 | 3/1970 | Fed. Rep. of Germany | 568/802 |
| 52-27730 | 3/1977 | Japan | 568/802 |
| 904697 | 8/1962 | United Kingdom | 568/802 |
| 1118821 | 7/1968 | United Kingdom | 568/802 |
| 1274653 | 5/1972 | United Kingdom | 568/802 |
| 176915 | 1/1966 | U.S.S.R. | 568/802 |

OTHER PUBLICATIONS

Denton, "Industrial and Engineering Chem.", vol. 42, No. 5, pp. 777-785, (1950).

Primary Examiner—Werren B. Lone
Attorney, Agent, or Firm—Abelman, Frayne & Rezac

[57] ABSTRACT

Benzene is catalytically oxidized in the vapor phase with oxygen in the presence of an alcohol to be converted to phenol. The catalyst used is represented by the formula: $M_a Ag_b P_c O_d$ wherein M is selected from zinc, titanium, zirconium, tin, bismuth and vanadium, Ag is silver, P is phosphorus and O is oxygen, and $a=1$, $b=0.005 \sim 5$ and $c=0$ to 6. Phenol is obtained at an enhanced yield even though the catalytic oxidation is carried out at a relatively low temperature as compared with conventional catalytic oxidation processes.

12 Claims, No Drawings

PROCESS FOR PREPARING PHENOL

BACKGROUND OF THE INVENTION (1) Field of the Invention

This invention relates to an improved process for preparing phenol by oxidizing benzene in the vapor phase with oxygen at an elevated temperature in the presence of a catalyst.

(2) Description of the Prior Art

Some proposals have been heretofore made to catalytically oxidize benzene in the vapor phase with oxygen at an elevated temperature in the absence of an alcohol to produce phenol. However, the yield of phenol produced by the heretofore proposed methods is very low, i.e., approximately 5%. For example, it is described in Japanese Laid-open Patent Application No. 61,439/73 to employ a catalyst substantially composed of copper phosphate and at least one metal oxide selected from iron oxide, manganese oxide, cobalt oxide and nickel oxide. The yields of phenol described therein are most 5.1%. Furthermore, it is described in Japanese Laid-open Patent Application No. 19,271/74 to employ a catalyst composed of copper borate. The yields of phenol described therein are at most 5.2%.

It also has been heretofore proposed to catalytically oxidize benzene in the vapor phase with oxygen at an elevated temperature in the presence of an alcohol to produce phenol. For example, it is described in British Pat. No. 1,274,653 that benzene is reacted in the vapor phase with oxygen in the presence of an alcohol at a temperature of 600° to 700° C. in a reactor having the internal surface coated with boric acid, thereby to produce phenol. The yield of phenol produced at a reaction temperature of 600° C. is very low, i.e., approximately 3%. Even the highest yield of phenol is 10.5%, which was achieved at a reaction temperature of 640° C. with a contact time of 4.0 seconds. Thus, it can be said that the catalytic oxidation carried out in the presence of an alcohol has some problems, namely, a high reaction temperature and/or a long contact time are necessary and the yields of phenol is still low.

SUMMARY OF THE INVENTION

It is, therefore, a primary object of the present invention to provide a process of the catalytic oxidation of benzene carried out in the vapor phase at an elevated temperature, by which phenol is produced at a high yield.

Other objects and advantages of the present invention will be apparent from the following description.

In accordance with the present invention, there is provided a process for preparing phenol wherein benzene is reacted in the vapor phase with oxygen at an elevated temperature in the presence of an alcohol and a catalyst, said catalyst being a composition consisting essentially of metal oxides and represented by the formula:

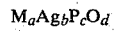

$M_a Ag_b P_c O_d$ wherein M is an element selected from the group consisting of zinc, titanium, zirconium, tin, bismuth and vanadium, Ag is silver, P is phosphorus and O is oxygen, and each of the subscripts "b" and "c" is a positive number indicating an atomic ratio of the respective element to the element M and falling within the following ranges: b=0.005 to 5, preferably 0.01 to 3 and c=0 to 6, preferably 0.1 to 3, provided that a=1, and "d" is a positive number satisfying the average valency of the respective elements and usually falling within the range of from 1 to 20.

DESCRIPTION OF THE PREFERRED EMBODIMENTS

In the catalyst composition used in the process of the present invention, it is believed that the elements M, Ag and P are present in the form of oxides. The elements expressed by "M", namely, zinc, titanium, zirconium, tin, bismuth and vanadium may be used either alone or in combination with each other. Phosphorus is an optional ingredient. It is, however, preferable that the catalyst used contains phosphorus because such catalyst results in a higher yield of phenol as compared with a catalyst containing no phosphorus.

When the respective elements M, Ag and P are present in amounts outside the ranges defined by the above-mentioned formula, the conversion of benzene, the selectivity to phenol or the yield of phenol is reduced.

The catalyst used in the process of the present invention may be prepared in any convenient manner by using, as the starting raw material, oxides, salts and other compounds, containing the above-specified elements. For example, an evaporation-to-dryness method, an immersion method and a co-precipitation method are conveniently employed.

An example of the procedure for the preparation of the catalyst will be described in the following. Predetermined amounts of a compound containing the element M and a compound containing phosphorus are mixed together in the presence of water. The mixture is dried at a temperature of from 100° to 200° C. and then, calcined at a temperature of from 350° to 700° C., preferably from 400° to 600° C., for a period of from 0.5 to 20 hours, preferably from 3 to 10 hours. The calcined product is pulverized into a powder. Then, the powder is mixed in the presence of water with a predetermined amount of a compound containing silver. The mixture is dried at a temperature of from 100° to 200° C. and then, calcined at a temperature of from 350° to 700° C., preferably from 400° to 600° C., for a period of from 0.5 to 20 hours, preferably from 3 to 10 hours to obtain the intended catalyst.

As illustrations of the starting raw materials for use in the preparation of the catalyst are enumerated, for example, zinc compounds such as zinc oxide, zinc carbonate, zinc chloride, zinc nitrate, zinc hydroxide and zinc sulfate; titanium compounds such as titanium (II, III and IV) chloride, titanium (II, III and IV) oxide and titanium (III and IV) sulfate; zirconium compounds such as zirconium (IV) oxide, zirconium (IV) chloride, zirconium (IV) hydroxide, zirconium (IV) nitrate and zirconium (IV) sulfate; tin compounds such as tin (IV) nitrate, tin (II and IV) oxide, tin (II and IV) chloride, tin (II) hydroxide and tin (II and IV) sulfate; bismuth compounds such as bismuth (III) nitrate, bismuth (III) hydroxide, bismuth (III) oxide and bismuth (II and III) chloride; vanadium compounds such as ammonium metavanadate, vanadium (II, III and IV) chloride, vanadium (III, IV and V) oxide and vanadyl sulfate; silver compounds such as silver nitrate, silver (I and II) oxide, silver carbonate, silver chloride, silver sulfate and silver oxalate; and phosphorus compounds such as diammonium hydrogen phosphate, metaphosphoric acid, phosphoric acid, ammonium phosphate, phosphorus pentachloride, phosphorus pentoxide and dimethyl phosphate.

The catalyst may be used either alone or in combination with a carrier. As carriers, those which are known for supporting conventional oxidation catalysts and favorably effect the reaction involved, such as silica, alumina, silica-alumina, carborundum, silicon carbide and diatomaceous earth may be used. In general, the size and shape of the catalysts are not particularly limited. The catalyst may be, for example, columnar, pellet-shaped or grain-shaped depending upon the conditions under which the catalyst is used.

Benzene used is catalytic oxidation according to the present invention may not necessarily be of a high purity. Benzene may contain minor amounts of other hydrocarbons such as, for example, toluene and xylene, which do not have unfavorable effects on the catalytic oxidation under the reaction conditions employed. Also, oxygen used in the catalytic oxidation according to the present invention need not necessarily be of a high purity. In general, oxygen-containing gases such as, for example, air or a gas mixture of pure oxygen with a diluent gas may conveniently be used. The amount of oxygen is usually in the range of from 0.05 to 8 moles, more preferably from 0.5 to 2 moles, per mole of benzene.

The alcohol used in the process of the present invention and its purity are not critical. Preferable alcohols are represented by the formula:

R—OH where R is an alkyl group having 1 to 4 carbon atoms, and include methyl alcohol, ethyl alcohol, propyl alcohol and butyl alcohol. The amount of the alcohol is usually in the range of from 0.01 to 10 moles, more preferably from 0.05 to 3 moles, per mole of benzene. When the catalytic oxidation of benzene is carried out in the absence of the alcohol, the yield of phenol is very low, but, with the use of the alcohol, the yield of phenol is enhanced to a great extent. When the amount of the alcohol is too large, the yield of phenol is reduced. It is preferable that the alcohol be supplied to the reaction system in the form of a mixed gas composed of the alcohol, benzene, oxygen and an optional diluent gas.

The gaseous feed comprised of benzene, an alcohol and oxygen may contain a diluent gas which does not influence the catalytic oxidation reaction involved. The diluent gas may be an inert gas such as, for example, steam, nitrogen, carbon dioxide or helium. Steam present in the gaseous feed makes the catalytic reaction proceed smoothly and makes the catalytic activity durable. Accordingly, it is generally preferred to incorporate steam in the gaseous feed. The amount of the diluent gas is preferably at least 0.5 moles per mole of benzene.

The catalytic oxidation reaction may be carried out generally in the range of from 450° to 700° C. It is to be noted, however, that phenol can be produced at a high yield even at a lower reaction temperature than conventionally employed reaction temperatures, namely, at a temperature of from about 500° to 620° C., particularly from about 500° to 600° C. The contact time is usually in the range of from 0.1 to 20 seconds, preferably from 1 to 5 seconds and more preferably from 2 to 4 seconds. The catalytic oxidation reaction may be carried out in a fixed bed or a fluidized bed.

According to the process of the present invention, phenol can be produced at a higher yield although the catalytic oxidation is carried out at a relatively low reaction temperature for a relatively short period, as compared with conventional catalytic oxidation processes wherein benzene is catalytically oxidized in the vapor phase with oxygen either in the presence or absence of an alcohol. The main by-products are carbon monoxide, carbon dioxide, ethylbenzene, toluene and styrene.

The present invention will be further described by the following examples and comparative examples, wherein the conversion of benzene, the selectivity to phenol and the yield of phenol were calculated in accordance with the following equations.

% conversion of benzene =
$$\frac{\text{moles of benzene consumed}}{\text{moles of benzene fed}} \times 100$$

% selectivity to phenol =
$$\frac{\text{moles of phenol produced}}{\text{moles of benzene consumed}} \times 100$$

% yield of phenol =
$$\frac{\text{moles of phenol produced}}{\text{moles of benzene fed}} \times 100$$

EXAMPLE 1

80.3 g of an aqueous 50% phosphoric acid [$H_3PO_4$] solution were gradually added to 50 g of a zinc oxide [ZnO] powder. The mixture was kneaded for 4 hours to obtain a white paste. Then, the paste was dried at a temperature of 120° C. for 12 hours in air, and then, calcined at a temperature of 500° C. for 5 hours. The calcined product was pulverized into a powder. To the powder was added a solution of 3.2 g of silver nitrate [$AgNO_3$] in 50 ml of water, followed by kneading for 3 hours. Then, the kneaded product was dried at a temperature of 120° C. for 12 hours and then, calcined at a temperature of 500° C. for 5 hours to prepare a catalyst. The atomic ratios of the elements Zn, Ag and P contained in the catalyst was as shown in Table I, below.

4 g of the catalyst were packed into a U-shaped tubular quartz reactor having an inner diameter of 15 mm. A gaseous mixture of benzene, methyl alcohol, steam, oxygen and nitrogen, the molar ratio of these ingredients being $C_6H_6$:MeOH:$H_2O$:$O_2$:$N_2$ = 1:0.34:1.82:1.60:12.60, was passed through the catalyst-packed reactor maintained at a temperature of 575° C. at a flow rate of 63 ml/min. The contact time was 2.8 seconds. Results are shown in Table I, below.

EXAMPLES 2 THROUGH 4

Following the same procedure as that employed in Example 1, catalysts were prepared wherein the amount of silver nitrate was varied so that the resultant catalysts contained Zn, Ag and P at the atomic ratios shown in Table I, below. Using these catalysts, the vapor phase catalytic oxidation of benzene was carried out under the same reaction conditions as those employed in Example 1. Results are shown in Table I, below.

EXAMPLES 5 THROUGH 11

Following the same procedure as that employed in Example 1, catalysts were prepared wherein titanium oxide [TiO$_2$], zirconium oxide [ZrO$_2$], titanium oxide [SnO$_2$], bismuth oxide [Bi$_2$O$_3$], vanadium oxide [V$_2$O$_5$], a mixture of bismuth oxide [Bi$_2$O$_3$] with zinc oxide [ZnO] and a mixture of bismuth oxide [Bi$_2$O$_3$] with tin oxide [SnO$_2$] were separately used instead of zinc oxide [ZnO]. The amounts of these oxides were such that the resultant catalysts contained M, Ag and P at the atomic ratios shown in Table I, below.

Using each of the catalysts so prepared, the catalytic oxidation of benzene was carried out under the same reaction conditions as those employed in Example 1. Results are shown in Table I, below.

TABLE I

| Ex. No. | Catalyst composition (atomic ratio) | | | Conversion of benzene (%) | Selectivity to phenol (%) | Yield of phenol (%) |
| --- | --- | --- | --- | --- | --- | --- |
| | M | Ag | P | | | |
| 1 | Zn = 1 | 0.06 | 0.7 | 41.6 | 61.5 | 25.6 |
| 2 | Zn = 1 | 0.02 | 1 | 41.2 | 60.9 | 25.1 |
| 3 | Zn = 1 | 0.02 | 2 | 40.8 | 62.0 | 25.3 |
| 4 | Zn = 1 | 0.06 | 0.1 | 42.9 | 55.8 | 23.9 |
| 5 | Ti = 1 | 0.02 | 1 | 44.8 | 54.5 | 24.4 |
| 6 | Zr = 1 | 0.02 | 1 | 43.2 | 53.7 | 23.2 |
| 7 | Sn = 1 | 0.01 | 1 | 42.8 | 55.1 | 23.6 |
| 8 | Bi = 1 | 0.06 | 0.5 | 41.6 | 59.4 | 24.7 |
| 9 | V = 1 | 3 | 1 | 45.3 | 50.6 | 22.9 |
| 10 | Bi = 1 Zn = 1 | 0.06 | 1 | 40.9 | 61.1 | 25.0 |
| 11 | Bi = 1 Sn = 1 | 0.06 | 2 | 42.4 | 57.8 | 24.5 |

(Reaction temperature = 575° C., contact time = 2.8 seconds)

EXAMPLE 12

A solution of 1.97 g of silver nitrate AgNO$_3$ in 25 ml of water was added to 50 g of a finely divided zinc oxide [ZnO] powder. The mixture was kneaded for 3 hours. The kneaded product was dried at a temperature of 120° C. for 12 hours in air and, then, calcined at a temperature of 500° C. for 5 hours to prepare a catalyst. The atomic ratio of Ag/Zn in the catalyst was as shown in Table II, below.

Using the catalyst so prepared, the catalytic oxidation of benzene was carried out under the same reaction conditions as those employed in Example 1 except that the reaction temperature was varied to 600° C. Results are shown in Table II, below.

EXAMPLES 13 THROUGH 17

Following the same procedure as that employed in Example 12, catalysts were prepared wherein titanium oxide [TiO$_2$], zirconium oxide [ZrO$_2$], tin oxide [SnO$_2$], bismuth oxide [Bi$_2$O$_3$] and vanadium oxide [V$_2$O$_5$] were separately used instead of zinc oxide [ZnO]. The amounts of these oxides were such that the resultant catalysts contained the element M and Ag at the atomic rations shown in Table II, below.

Using each of the catalysts so prepared, the catalytic oxidation of benzene was carried out under the same reaction conditions as those employed in Example 12 wherein the reaction temperature and the contact time were varied as shown in Table II, below (in Examples 15, 16 and 17, only the reaction temperature was varied). Results are shown in Table II.

TABLE II

| Ex. No. | Catalyst composition [Ag/M(atomic ratio)] | | Reaction temperature (°C.) | Contact time (second) | Conversion of benzene (%) | Selectivity to phenol (%) | Yield of phenol (%) |
| --- | --- | --- | --- | --- | --- | --- | --- |
| | Ag/M | M | | | | | |
| 12 | 0.02 | Zn | 600 | 2.8 | 37.5 | 41.4 | 15.5 |
| 13 | 0.02 | Ti | 550 | 3.0 | 40.3 | 49.1 | 19.8 |
| 14 | 0.02 | Zr | 570 | 3.0 | 38.4 | 48.7 | 18.7 |
| 15 | 0.01 | Sn | 570 | 2.8 | 40.8 | 42.2 | 17.2 |
| 16 | 0.06 | Bi | 525 | 2.8 | 37.1 | 43.9 | 16.3 |
| 17 | 3 | V | 575 | 2.8 | 43.9 | 36.2 | 15.9 |

EXAMPLE 18

Using the same catalyst as that employed in Example 1, the catalytic oxidation of benzene was carried out under the same reaction conditions as those employed in Example 1 except that ethyl alcohol was used instead of methyl alcohol.

The results were as follows.
Conversion of benzene:43.9%.
Selectivity to phenol:55.8% and
Yield of phenol:24.5%

COMPARATIVE EXAMPLE 1

Using the same catalyst as that employed in Example 1, the catalytic oxidation of benzene was carried out under the same reaction conditions as those employed in Example 1 except that no methyl alcohol was incorporated in the gaseous mixture to be fed into the reactor. Results are shown in Table III, below.

COMPARATIVE EXAMPLE 2

Using as a catalyst the same calcined product as that obtained from zinc oxide and an aqueous phosphoric acid solution in Example 1, the catalytic oxidation of benzene was carried out under the same reaction conditions as those employed in Example 1 except that the reaction temperature and the contact time were varied to 600° C. and 3 seconds, respectively. The atomic ratio of Zn:P was as swhon in Table III, below. Results are shown in Table III.

COMPARATIVE EXAMPLE 3

Following the same procedure as that employed in Example 1, a catalyst was prepared except that the amount of silver nitrate was varied so that the resultant catalyst had the atomic ratio of Zn:Ag:P shown in Table III, below, namely, the catalyst contained silver in an amount not satisfying the hereinbefore-mentioned formula.

Using the catalyst so prepared, the catalytic oxidation of benzene was carried out under the same reaction conditions as those employed in Example 1. Results are shown in Table III, below.

COMPARATIVE EXAMPLE 4

147 g of an aqueous 50% phosphoric acid solution were added to 39.8 g of copper oxide [CuO]. The mixture was kneaded at a temperature of 150° C. for 5 hours. Thereafter, the kneaded product was calcined at a temperature of 500° C. for 5 hours in air to prepare copper phosphate [Cu$_2$(PO$_4$)$_3$]. 20 g of the prepared copper phosphate were mixed with 20 g of manganese oxide [MnO$_2$] and a minor amount of water, followed by kneading for 5 hours. The kneaded product was dried at a temperature of 150° C. for 5 hours and, then, calcined at a temperature of 500° C. for 5 hours in air to prepare a catalyst. The atomic ratio of Cu:Mn:P contained in the catalyst was as shown in Table III, below.

Using the catalyst mentioned above, the catalytic oxidation of benzene was carried out under the same reaction conditions as those employed in Example 1 except that the reaction temperature was varied to 580° C. Results are shown in Table III, below.

COMPARATIVE EXAMPLES 5 THROUGH 7

Zinc oxide [ZnO], bismuth oxide [Bi$_2$O$_3$] and vanadium oxide [V$_2$O$_5$] were separately calcined at a temperature of 550° C. for 5 hours in air to prepare catalysts.

Using each catalyst, the catalytic oxidation of benzene was carried out under the same reaction conditions as those employed in Example 1 except that the reaction temperature was varied to 525° C. in Comparative Example 6. Results are shown in Table III, below.

TABLE III

| Comp. Ex. No. | Catalyst composition (atomic ratio) | Reaction temperature (°C.) | Conversion of benzene (%) | Selectivity to phenol (%) | Yield of phenol (%) |
|---|---|---|---|---|---|
| 1 | Zn:Ag:P = 1:0.06:0.7 | 575 | 7.2 | 6.0 | 0.4 |
| 2 | Zn:P = 1:0.7 | 600 | 43.0 | 30.0 | 12.9 |
| 3 | Zn:Ag:P = 1:0.0001:0.7 | 575 | 27.1 | 34.3 | 9.3 |
| 4 | Cu:Mn:P = 1:2:1.5 | 580 | 16.9 | 15.1 | 2.6 |
| 5 | ZnO | 575 | 18.0 | 30.0 | 5.4 |
| 6 | Bi$_2$O$_3$ | 525 | 14.9 | 28.1 | 4.2 |
| 7 | V$_2$O$_5$ | 575 | 16.3 | 15.8 | 2.6 |

We claim:

1. In a process for preparing phenol wherein benzene is reacted in the vapor phase with oxygen at an elevated temperature in the presence of a catalyst, said improvement comprising effecting the oxidation of benzene in the presence of an alcohol and by using as the catalyst a composition consisting essentially of metal oxides and represented by the formula:

$$M_a Ag_b P_c O_d$$

wherein M is an element selected from the group consisting of zinc, titanium, zirconium, tin, bismuth and vanadium, Ag is silver, P is phosphorus and O is oxygen, and each of the subscripts "b" and "c" is a positive number indicating an atomic ratio of the respective element to the element M and falling within the following ranges: b=0.005 to 5 and c=0 to 6, provided that a=1, and "d" is a positive number satisfying the average valency of the respective elements.

2. A process according to claim 1, wherein the atomic ratios of the respective elements are such that the subscripts "b" and "c" are positive numbers falling within the ranges: b=0.01 to 3 and c=0.1 to 3, provided that a=1.

3. A process according to claim 1, wherein the relative amount of oxygen to benzene is in the range of from 0.05 to 8 moles per mole of benzene.

4. A process according to claim 1, wherein the relative amount of oxygen to benzene is in the range of from 0.5 to 2 moles per mole of benzene.

5. A process according to claim 1, wherein the alcohol is represented by the formula:

ROH wherein R is an alkyl group having 1 to 4 carbon atoms.

6. A process according to claim 1, wherein the relative amount of the alcohol to benzene is in the range of from 0.01 to 10 moles per mole of benzene.

7. A process according to claim 1, wherein the relative amount of the alcohol to benzene is in the range of from 0.05 to 3 moles per mole of benzene.

8. A process according to claim 1, wherein the alcohol, benzene and oxygen are fed into a reactor in the form of a gaseous mixture thereof together with at least 0.5 mole of steam per mole of benzene.

9. A process according to claim 1, wherein the catalytic oxidation of benzene is carried out at temperature of from 450° to 700° C. for a period of from 0.1 to 20 seconds.

10. A process according to claim 1, wherein the catalytic oxidation of benzene is carried out at a temperature of from about 500° to 620° C. for a period of 1 to 5 seconds.

11. A process according to claim 1, wherein the catalyst composition is a calcined resisue of a mixture of the respective element-containing compounds, said element-containing compound being in the form of an oxide, a salt or a mixture thereof.

12. A process according to claim 11, wherein the calcined residue is obtained by calcining the mixture of the respective element-containing compounds at a temperature of from 350° to 700° C. for 0.5 to 20 hours.

* * * * *